(12) United States Patent
Brunet et al.

(10) Patent No.: US 6,803,586 B1
(45) Date of Patent: Oct. 12, 2004

(54) FLUID TREATMENT SYSTEM AND METHOD OF TREATING FLUID

(75) Inventors: Robert A. H. Brunet, Mount Brydges (CA); George Traubenberg, London (CA); Ted Mao, Brampton (CA); Feraz Hosein, Brooks (CA)

(73) Assignee: Trojan Technologies Inc. (CA)

( * ) Notice: Subject to any disclaimer, the term of this patent is extended or adjusted under 35 U.S.C. 154(b) by 0 days.

(21) Appl. No.: 09/567,051

(22) Filed: May 8, 2000

Related U.S. Application Data (60) Provisional application No. 60/188,189, filed on Mar. 10, 2000.

(51) Int. Cl.[7] .................................................. A61L 2/10
(52) U.S. Cl. ..................... 250/434; 250/373; 422/186.3; 422/24; 422/906
(58) Field of Search ................................. 250/434, 373, 250/431, 372, 432 R, 435, 436, 438; 422/186.3, 24, 906

(56) References Cited

U.S. PATENT DOCUMENTS

| | | | | |
|---|---|---|---|---|
| 4,103,167 A | * | 7/1978 | Ellner | 250/432 |
| 5,151,174 A | | 9/1992 | Wiesmann | 210/97 |
| 5,200,156 A | | 4/1993 | Wedekamp | 422/186.3 |
| 5,208,461 A | | 5/1993 | Tipton | 250/436 |
| 5,332,388 A | * | 7/1994 | Schuerch et al. | 422/291 |
| 5,624,573 A | | 4/1997 | Wiesmann | 210/748 |
| 6,139,726 A | * | 10/2000 | Greene | 210/175 |
| 6,264,836 B1 | * | 7/2001 | Lantis | 210/188 |

FOREIGN PATENT DOCUMENTS

| | | |
|---|---|---|
| DE | 27 53 263 | 5/1979 |
| DE | 42 06 596 A1 | 9/1993 |
| DE | 93 20 594 | 2/1995 |
| DE | 198 07 540 A1 | 8/1999 |
| EP | 1 038 835 A1 | 9/2000 |
| JP | 11-47740 | 2/1999 |
| WO | WO 00/55095 | 9/2000 |

OTHER PUBLICATIONS

Patent Abstracts of Japan, vol. 1999, No. 05, May 31, 1999 & JP 11 047740 A, Feb. 23, 199.

* cited by examiner

*Primary Examiner*—John R. Lee
*Assistant Examiner*—Zia R. Hashmi
(74) *Attorney, Agent, or Firm*—Katten Muchin Zavis Rosenman

(57) ABSTRACT

It is often desirable to operate ultraviolet (UV) water treatment systems at high fluid velocities; such as, when low UV doses are required, the UV transmittance of the water being treated is high, or when a high intensity radiation source is used. The operation of an open channel UV fluid treatment system at high fluid velocity causes a disproportionate amount of water to pass through the relatively low intensity region above the top lamp. This results in non-uniform UV dose delivery and poor reactor performance. In one embodiment of the invention, by elevating the inlet to the irradiation zone of the fluid treatment system with respect to the outlet, the amount of water that passes above the top lamp can be minimized, improving overall system performance. The means of elevation can consist of a step or slope in the channel, or a combination of both. Depending on the magnitude of elevation, an increase in maximum velocity of approximately two times can be obtained. In practice, a means must be provided to prevent damage to the radiation sources of the elevated banks that become exposed during periods of low flow. This can consist of either a mechanism for switching off the affected lamp when low water level or high temperature is detected, or a means of lamp cooling.

73 Claims, 5 Drawing Sheets

FLOW
(1334L/min)

1% SLOPE

Figure 9

FLOW
(1389L/min)

2% SLOPE

FLUID TREATMENT SYSTEM AND METHOD OF TREATING FLUID

This application claims benefit of Provisional Appln. No. 60/188,189, filed Mar. 10, 2000.

BACKGROUND OF THE INVENTION

1. Field of the Invention

In one of its aspects, the present invention relates to a fluid treatment system, more particularly an ultraviolet (UV) water treatment system in an open channel, the performance of which is improved by mitigating flow through the low intensity region of the reactor above the top lamp when the system is operated at high fluid velocities. In another aspect of the invention, this is achieved by designing elevation differences between the upstream and downstream ends of the system while obviating or mitigating top lamp overheating due to exposure during periods of low flow.

2. Description of the Prior Art

UV disinfection systems are used in wastewater and drinking water plants to control microbial growth. UV of a wavelength which can be absorbed by cellular nucleotides causes cross-linking, or dimerization, of RNA and DNA, preventing the micro-organisms from replicating and effectively disinfecting the water (Jagger, J. *Introduction to research in ultraviolet photobiology*. Englewood Cliffs, N.J.: Prentice-Hall Inc., 1967; p.69–73). This technology has been successfully applied commercially in large scale systems since 1981 (U.S. Pat. No. 4,482,809).

Open channels are commonly used to transport or convey large volumes of fluid by gravity and are typically made of concrete. Gravity is used to avoid the high pumping costs that would be incurred if the transport channels were closed and pressurized. Routine cleaning maintenance is made easier by having access to the channel through the open top. Thus, in some applications, it is advantageous when designing a UV disinfection system to make use of conventional open fluid channels to minimize reactor costs and provide for ease of maintenance while still maintaining a gravity flow regime to avoid incurring pumping cost.

Figure 1:
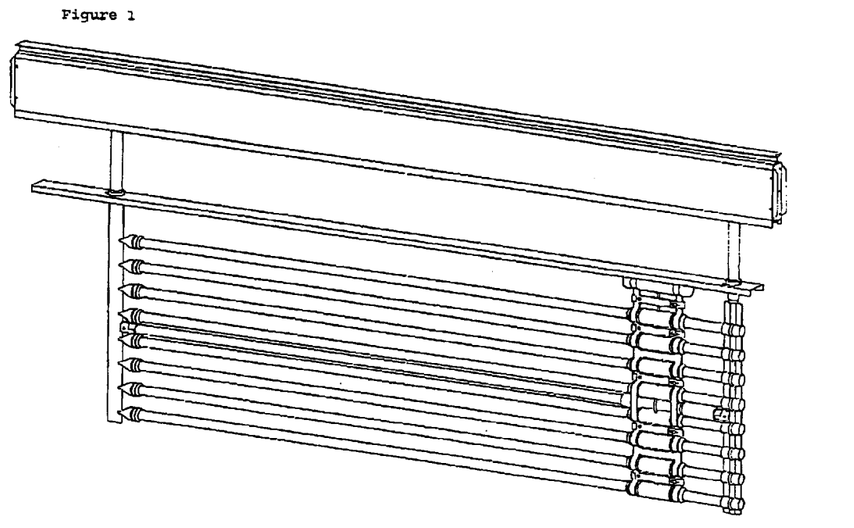
FIG. 1 shows a perspective view of a modular assembly of UV radiation source modules, complete with an automated chemical-mechanical cleaning system, similar to the one described in copending U.S. patent application Ser. No. 09/258,143.
Figure 2:
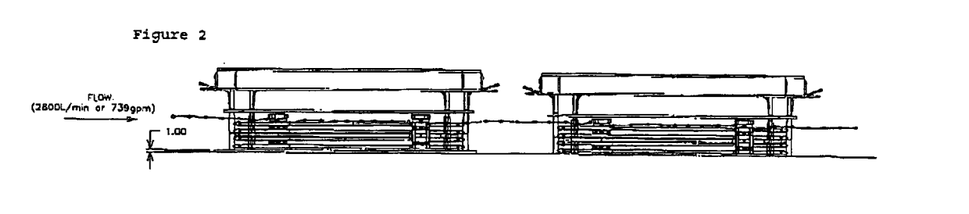
FIG. 2 shows an experimentally derived water level profile through two banks of modular assemblies in hydraulic series at 2800 L/min with the upstream bank on a 1" step.
Figure 3:
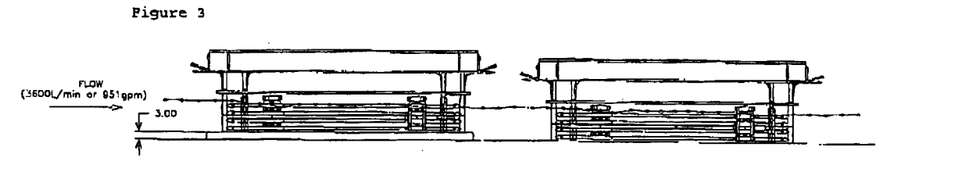
FIG. 3 shows an experimentally derived water level profile through two banks of modular assemblies in hydraulic series at 3600 L/min with the upstream bank on a 3" step.
Figure 4:
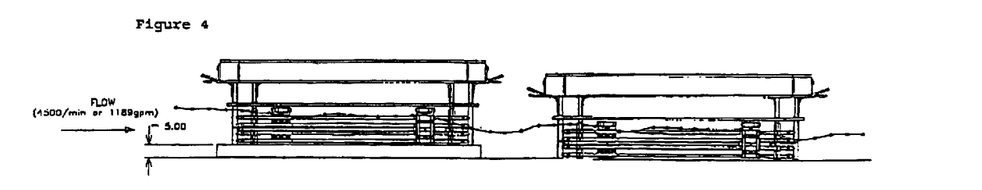
FIG. 4 shows an experimentally derived water level profile through two banks of modular assemblies in hydraulic series at 4500 L/min with the upstream bank on a 5" step.
Figure 5:
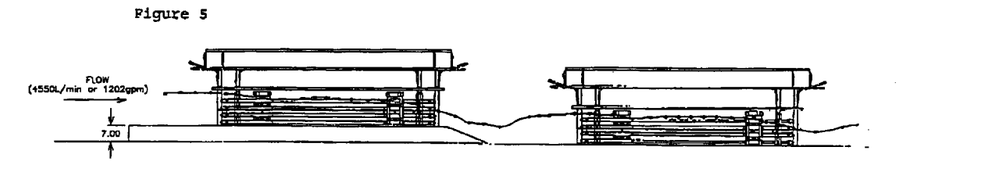
FIG. 5 shows an experimentally derived water level profile through two banks of modular assemblies in hydraulic series at 4550 L/min with the upstream bank on a 7" step.

Open channel UV disinfection systems for water treatment typically consist of a number of modular assemblies (also known as radiation source modules) arranged in parallel across the width of the fluid canal (U.S. Pat. No. 4,482,809, copending U.S. patent application Ser. No. 09/185,813 (filed Nov. 3, 1998) and copending U.S. patent application Ser. No. 09/258,143 (filed Feb. 26, 1999)). An example of such an assembly is shown in FIG. 1. These assemblies may consist of a number of radiation source modules (1), such as UV lamps enclosed in quartz sleeves, that are substantially parallel to the direction of fluid flow. The modules may be lifted from the channel for routine maintenance, such as sleeve cleaning and lamp replacement. In some cases, an automatic cleaning mechanism is present, consisting of a wiper canister (2) and a drive mechanism (3). The fluid flows past the modules in a relatively unrestricted fashion under the influence of gravity, with a minor difference in water level between the upstream and downstream ends required to allow the water to pass the submerged geometry. This water level difference is dependent on a number of factors, including the complexity of the submerged geometry, the horizontal spacing between modules, the fluid velocity and the like.

The effectiveness of an open channel UV system depends on its ability to deliver the dose of UV required to reach the target disinfection level to each fluid element. The UV dose is defined as the product of UV intensity and reactor retention time, and is normally expressed in mWs/cm$^2$. The inactivation of micro-organisms follows a first order kinetic expression proportional to the UV dose (Jagger, J. *Introduction to research in ultraviolet photobiology*. Englewood Cliffs, N.J.: Prentice-Hall Inc., 1967; p.69–73). Therefore, the delivery of a uniform dose to all micro-organisms as they pass through the reactor improves reactor efficiency.

As UV passes through a fluid, its intensity at a given point depends on the fluid transmittance of the wavelength in question. The most common germicidal wavelength used is 254 nm, since this wavelength is produced effectively by conventional low pressure mercury arc lamps. Wastewater often exhibits low transmittance of germicidal wavelengths, resulting in a decrease in UV intensity as light travels away from the lamps. This leads to regions of lowest UV intensity between lamps. A certain spacing, dependent on water quality and lamp type is desirable to ensure adequate dose delivery and reactor performance.

The residence time required for adequate dose delivery depends on UV intensity. For poor water quality, UV transmittance and average UV intensity are low, usually requiring relatively long residence times within the reactor to maintain adequate dose. This is typically accomplished by designing the UV disinfection system with banks of UV modules disposed serially. Conversely, with good water quality or high intensity radiation sources, residence time is normally decreased to achieve the same dose. This is usually accomplished by designing relatively narrow fluid channels, decreasing the amount of UV equipment required as compared with a system installed in a wide channel. This results in relatively high fluid velocities past the modules, leading to significant differences in water level between the upstream and downstream ends of the system.

Since UV radiation from each lamp only penetrates a certain distance into the fluid, each lamp can effectively treat a layer of water around it, usually equal to approximately one half the spacing between lamps. When large water level differences cause the layer of water above the top lamp to exceed this critical value, the excess water travels through a zone of relatively low UV intensity, exiting the irradiation zone with lower than adequate dose. This fluid "short circuit" leads to non-uniform dose distribution, resulting in micro-organisms escaping essentially untreated, leading to poor overall reactor performance.

It is desirable to have a reactor which obviates or mitigates water level differences that lead to a "short circuit" above the top lamp over a relatively wide range of water qualities and flow rates. The submerged geometry is fixed by the design of the modular assemblies and usually cannot easily be modified without comprising equipment functionality. Horizontal spacing often cannot be increased without producing regions of low UV intensity in the reactor. For good water quality or high intensity radiation sources, it is therefore usually important to operate a UV disinfection system at high fluid velocities for the reasons described above.

It would be desirable to have a fluid treatment system capable of obviating or mitigating a "short circuit" effect over the top lamp of a UV disinfection system when operated at high fluid velocities using elevation differences between the upstream and downstream ends of the reactor.

SUMMARY OF THE INVENTION

It is an object of the invention to provide a novel fluid treatment system which obviates or mitigates at least one of the above-mentioned disadvantages of the prior art.

Accordingly, in one of its aspects, the present invention provides a fluid treatment system comprising at least one radiation source disposed in an open irradiation zone, the irradiation zone have a fluid inlet which is elevated with respect to a fluid outlet.

In another of its aspects, the present invention provides a fluid treatment system comprising an array of radiation sources disposed in an open channel, an upstream end of the open channel adjacent an upstream end of the array being elevated with respect to a downstream end of the open channel adjacent a downstream end of the array.

In yet another of its aspects, the present invention provides a fluid treatment system comprising a first irradiation zone and a second irradiation zone disposed at different heights with respect to one another such that the fluid level is substantially normalized with respect to the top of each of the first irradiation zone and the second irradiation zone.

In yet another of its aspects, the present invention provides a fluid treatment system comprising a plurality of serially disposed irradiation zones which are elevated with respect to one another thereby substantially normalizing the fluid level with respect to the top of each irradiation zone.

In yet another of its aspects, the present invention provides a fluid treatment system comprising a first irradiation zone and a second irradiation zone disposed at different heights with respect to one another such that the fluid level is substantially normalized with respect to the top of each of the first irradiation zone and the second irradiation zone.

In yet another of its aspects, the present invention provides a fluid treatment system comprising a canal for receiving a fluid to be treated, a first upstream irradiation zone and a second downstream irradiation zone which is stepped with respect to the first upstream irradiation zone.

A UV disinfection system, consisting of multiple banks of modular assemblies in hydraulic series, may be constructed using different elevations for each bank. This can be accomplished using a step for the upstream bank and/or by placing both banks on a slope. Water level differences resulting from fluid flow past submersed bodies ("head loss") propagate upstream from a fixed level point, such as a gate, weir or the like.

In one embodiment, a step elevates an upstream bank relative to a downstream bank to prevent an excessively high water level above the top lamp of the upstream bank. Preferably, the step comprises a height in the range of from about 0.5 to about 7.0 inches, more preferably in the range of from about 0.5 to about 5.0 inches, even more preferably in the range of from about 1.0 to about 4.0 inches, most preferably in the range of from about 1.0 to about 3.0 inches.

A slope can also be used to provide elevation of the upstream bank, so that little or no change in water level is desirable to cause fluid to flow. Preferably, the sloped surface comprises a slope of at least about 0.2%, more preferably in the range of from about 0.2% to about 6.0%, even more preferably in the range of from about 0.2% to about 3.0%, even more preferably in the range of from about 0.5% to about 2.5%, most preferably in the range of from about 1.0% to about 2.0%. As those of skill in the art will recognize, the "slope" be readily determined by dividing the rise of the sloped surface by the run of the sloped surface.

The size of step or angle of slope may be selected by the combination of design velocity and submerged geometry for a given treatment system. As velocity increases or submerged geometry becomes more restrictive, the potential energy required for fluid flow increases, mandating a larger step height or angle of slope. When flow rate drops below the design value, the top lamps of the elevated bank can become exposed, resulting in high lamp temperatures and premature lamp failures. Cooling of the affected lamps can be accomplished by directing a fluid, such as water or air, to flow over the lamps, thereby removing heat and reducing lamp temperature. Alternatively, the affected lamps may be switched off to reduce energy consumption and prevent premature high temperature failure from occurring.

Preferably, the term "fluid inlet", when used in the context of the irradiation zone, means any plane located upstream of the radiation source(s) and through which fluid may flow. Further, the term "fluid outlet", when used in the context of the irradiation zone, means any plane located downstream of the radiation source(s) and through which fluid may flow.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Differences in elevation are commonly employed in open channel fluid engineering to cause water to flow from region to region under the influence of gravity. These level differences can be abrupt, such as steps in the fluid channel, or gradual, such as slopes. The use of steps and slopes in open channel fluid engineering is well documented (Tchobanoglous, G. *Wastewater Engineering: Collection and Pumping of Wastewater.* New York, N.Y.: McGraw-Hill, 1981; pp. 10–11, pp. 44–45. Henderson, F. M. *Open Channel Flow.* New York, N.Y.: MacMillan Publishing Co., 1966; pp. 30–31; pp. 106–107; pp. 212–213). However, when fluid obstruction elements (such as UV disinfection equipment) are placed in the fluid channel, the hydraulics (e.g., head loss, velocity, UV reactor efficiency, etc.) of the fluid, as set out in these general references, are significantly affected.

Stepped channels normally induce more fluid turbulence and cause a greater amount of overall energy loss than do sloped channels, which provide more gradual energy changes. Either method of construction leads to a total head loss that is greater than or equal to the head loss experienced by a fluid flowing through a horizontal channel. The object of the present invention is not necessarily to reduce the total head loss across UV disinfection equipment, but rather to maintain a constant water level through the UV disinfection reactor when operated at high fluid velocity, thereby improving system performance under these conditions.

When a UV system is installed in an open channel, a device is usually installed downstream of the system to provide resistance to flow and cause the lamps to be submerged. This device is typically some type of gate, weir or the like. Level differences needed for fluid to flow past the equipment propagate upstream in reference to this fixed minimum height. Under high velocity conditions, when water level differences are large, the upstream banks of a multi-bank system are therefore most susceptible to "short circuiting" over the top lamp. By raising each bank with respect to the one downstream of it, such as by putting it on a step, the top lamps are kept closer to the water surface, thereby preserving the critical water layer that can be treated by a single lamp and maintaining adequate dose delivery to substantially all of the top layer of the fluid.

Experiments were conducted using a UV system with four radiation source modules similar to the one illustrated in FIG. 1 in each of two banks in hydraulic series, with 3" spacing between modules. Alternating modules were turned 180° to the direction of flow and staggered by 7" to align the arc lengths. Flow rates were varied in order to produce a range of velocities from 0.59 m/s to 1.09 m/s. Step heights of 1, 3, 5, and 7" were used, as shown in FIGS. 2, 3, 4, and 5, respectively, to elevate the upstream bank in order to prevent a "short circuit" from forming over the top lamp. Previous testing showed that no step was needed for velocities less than 0.5 m/s. The 7" step created relatively severe flow conditions at velocities greater than 1 m/s, most noticeably between banks. During testing, the spacing between banks was increased to seven feet to allow for flow stabilization upstream of the second bank. Under these conditions, water level was still changing rapidly due to waves, making accurate measurements difficult. An increase in the distance between banks might allow a 7" step to be used.

FIGS. 2 through 5 show representative water level profiles with different step heights. As the flow rate increased, a larger step height (3) was used for the upstream bank (1). The downstream bank (2) is shown on the channel bottom. At least thee different flow rates were used with each step height. A representative water level profile (4) derived from experimental data is shown on each Figure for a given set of test conditions. As step height was increased, the flow rate that could be treated without a "short circuit" forming over the top lamp increased. A summary of data collected from all experiments, showing the water level as measured at the midpoint of the upstream and downstream banks, is presented in Table 1. Note that water level is measured with reference to the channel bottom, so levels measured for the upstream bank include the step height.

The target water level through the arc length of the UV lamp is 12". The minimum water level that covers at least some portion of the lamp is 10". The data shows that as flow rate (velocity) increases, the desired step height also increases to maintain the 12" maximum water level limitation. The velocity through the first bank is typically slightly higher than for the second bank. This is due to reduced water level over the step as compared with the rest of the channel. The higher velocity for the upstream bank often led to a "hydraulic jump" forming as the fluid left the region between modular assemblies. These jumps form due to the transition from sub-critical to super-critical flow, which causes the fluid to loose energy and return to sub-critical conditions. Hydraulic jumps often manifest themselves as standing waves. These standing waves lead to the high water level difference that can sometimes be seen across the first bank and across the second bank at high flow rates.

The total head lost is the sum of water level differences for each bank, whereas the total water level change is the difference in water level across both banks. The total head lost is always higher than the total water level difference. This illustrates that the objective of using a step is not necessarily to minimize the total amount of energy loss through both banks of a multi bank UV system, but rather to control water level through the arc length in order to improve disinfection performance at high fluid velocity.

By interpreting the data in Table 1, it is possible to determine the velocity range for which a step of a certain height is applicable. This is summarized in Table 2. It is apparent that by using a step of the appropriate height, the range of velocities that can be used in an open channel UV system while minimizing or eliminating formation of "short circuits" over the top lamp is approximately doubled.

Water flow occurs as potential energy is converted to kinetic energy. The rate of fluid flow is determined by the product of the wetted cross sectional area of the channel and the fluid velocity. As water flows through a horizontal channel, its level decreases as it looses potential energy. For a constant flow of water, the velocity must increase as the level decreases, since potential energy is being converted to kinetic energy.

A channel built with a slope has one end higher than the other. As fluid flows through the channel, the difference in elevation of the channel bottom causes a change in potential energy, meaning that less change in water level is needed to provide kinetic energy for fluid flow. The desired slope to maintain water level constant depends on the amount of kinetic energy needed to maintain constant fluid velocity. As objects are added to the channel which increase frictional losses, a greater channel slope is desirable to minimize any negative effects of changes in water level.

Installing a UV disinfection system on a sloped channel causes frictional losses. Frictional losses are a function of the submerged geometry and the fluid velocity. For a given flow rate and UV system configuration, there is a preferred channel slope which causes little or no change to the level of water as it passes through the system. The system configuration refers to the channel width, the spacing between modular assemblies, and the design of all components beneath the waterline. These determine the total energy loss as water passes through the system and therefore the required slope to maintain constant water level.

Figure 6:
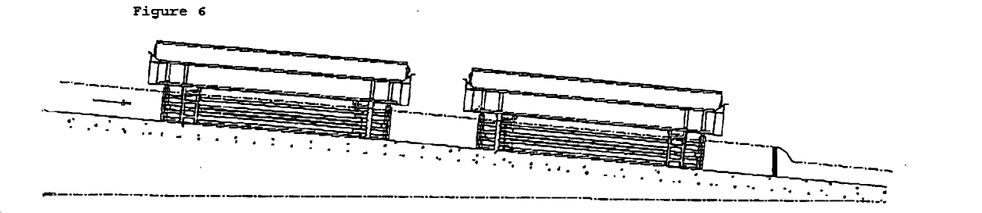
FIG. 6 shows a conceptual representation of two banks of modular assemblies in hydraulic series on a slope with velocity matched to the angle of the slope such that the water level profile is approximately constant.

FIG. 6 is a conceptual representation of a two bank system designed with a sloped channel bottom. Flow travels in the direction of declined slope, and is indicated by an arrow (5). The water level profile (3) across the upstream bank (1) and downstream bank (2) is virtually parallel with the channel bottom (4) if the slope is chosen correctly for the design flow rate. A weir (7) is included downstream of the second bank to maintain water level across the lamps. The slope angle (6) shown in the conceptual drawing is much steeper than required for the typical range of flow rates encountered in a wastewater treatment plant.

Experiments were performed with a single bank of three UV modules spaced 3" apart in a sloped channel as described hereinabove. Slope was varied from −1% to 6% (positive slope in the declined direction) by adjustment of a jack mechanism. Through varying the flow rate and depth of water in the channel, velocities ranging from 0.3 to 0.9 m/s were tested in fifty-seven separate experiments. The results of these experiments were used to predict the optimum slope desirable to minimize the occurrence of excessive water layers over the top lamp for a given combination of velocity and submerged geometry.

Table 3 shows the change in water level incurred at the velocities indicated with no slope applied to the channel bottom. As expected, as velocity was increased, the water level change also increased, since the frictional loss is proportional to the square of velocity. For this lamp spacing and resultant submerged geometry, a water level change greater than 1" is considered undesirable, since it leads to "short circuiting" of water above the top lamp in the upstream banks of a multi-bank system. Velocities greater than approximately 0.5 m/s result in this condition and are undesirable.

For the highest velocity that could be obtained, the slope of the channel bottom was increased in order to observe the effect on water level differences. Since the maximum flow was limited by the capability of the pump, the downstream weir height was lowered to reduce the available cross sectional area for flow, thereby increasing the velocity in the channel. The lower water level caused only the bottom two lamps of the four lamp modular assembly to be covered with water; since the sloped channel tests were conducted without turning lamps on, exposure of the top lamps was not a concern.

Figure 7:
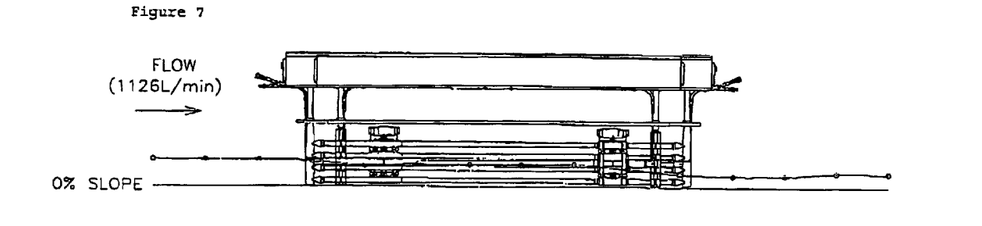
FIG. 7 shows an experimentally derived water level profile through one bank of modular assemblies at 1126 L/min on a 0% slope with only the bottom two lamps submerged.
Figure 8:
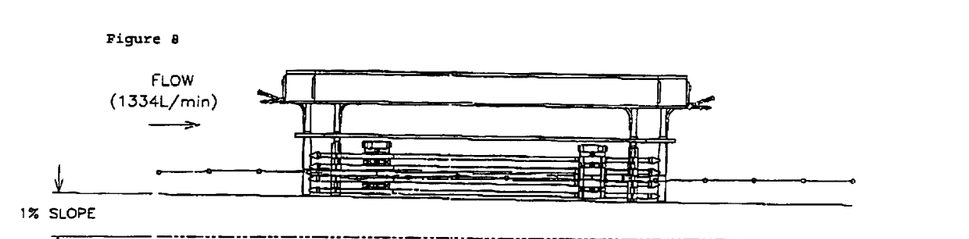
FIG. 8 shows an experimentally derived water level profile through one bank of modular assemblies at 1334 L/min on a 1% slope with only the bottom two lamps submerged.
Figure 9:
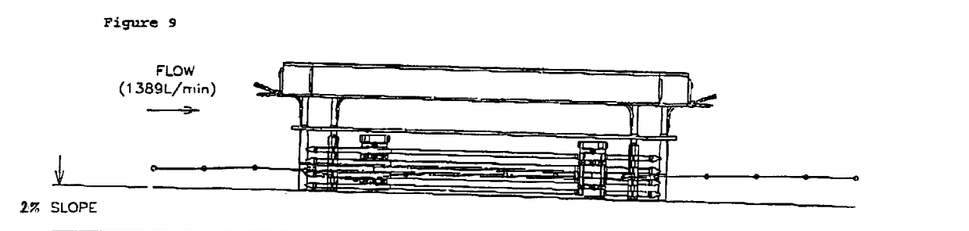
FIG. 9 shows an experimentally derived water level profile through one bank of modular assemblies at 1389 L/min on a 2% slope with only the bottom two lamps submerged.

Data from the high velocity experiments is shown in FIGS. 7 through 9. The flow rate (1) and slope (2) are shown on each drawing for a single bank of three modular assemblies (3) as discussed above. The water level profile (4) derived from experimental data is also shown. As discussed above, the top two lamps (5) and (6) are exposed during each test in order to obtain high velocity. A summary of results obtained from this series of tests is presented in Table 4.

For a velocity that produces an unacceptable water level difference with no slope, applying a 1% channel slope results in nearly no loss in water level, or a flow profile nearly parallel to the channel bottom throughout the UV reactor. A constant water level profile provides uniform delivery of UV dose to all water flowing through the reactor, resulting in superior disinfection performance. As slope was increased to 2%, the negative water level difference implies that the level downstream of the reactor was actually higher than the upstream level. This shows that a 2% slope provides excessive potential energy change for this combination of velocity and submerged geometry, again resulting in excessive water level differences and "short circuiting" over the top lamp. For this submerged geometry, a velocity of 0.9 m/s is optimally treated with approximately a 1% slope.

Changing the submerged geometry results in a different required slope for a given velocity. Table 5 shows data collected with the center modular assembly oriented 180° and staggered 2.5" downstream with respect to the other two modules. This results in the cleaning mechanisms of adjacent modular assemblies not being directly beside each other, providing less overall restriction to flow through the system. Without any slope, the water level difference decreased from 3.1" to 1.5" at the same fluid velocity. A 1% slope resulted in a negative water level difference, showing that this slope was too great for the given combination of velocity and submerged geometry. The slope required to prevent a "short circuit" from forming over the top lamp is therefore a function of not only the velocity, but the submerged geometry of equipment installed in the channel, and decreases as restriction to fluid flow decreases.

Figure 10:
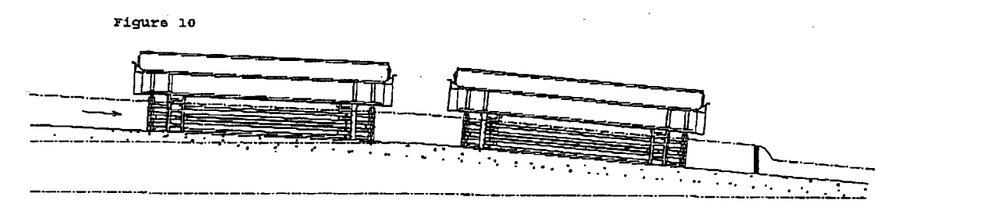
FIG. 10 shows a conceptual representation of two banks of modular assemblies in hydraulic series on a compound slope, the upstream bank having less resistance to flow than the downstream bank, with the angle of slope for each bank chosen in order to produce a water level profile that is approximately constant through each bank.

If different system configurations are used in each bank of a multi-bank system, the desired slope for each bank changes. FIG. 10 shows a system built with the upstream bank (1) built with one slope angle (3) and the downstream bank (2) built with a steeper slope angle (4). In the embodiment shown, the less restrictive submerged geometry is for the upstream bank (1). The water level profile (5) is approximately parallel to the channel bottom for each sloped section (3) and (4) if the angle is correctly chosen for the given combination of submerged geometry and flow rate. The same concepts could also be applied with the less restrictive geometry and the smaller slope angle downstream.

Figure 11:
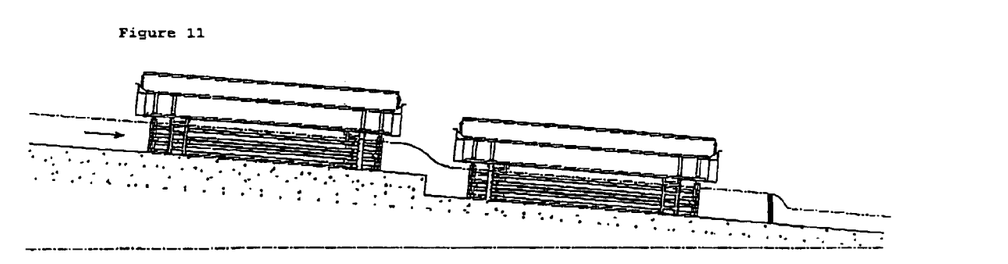
FIG. 11 shows a conceptual representation of two banks of modular assemblies in hydraulic series on a slope, with the step height chosen to prevent "short circuiting" above the top lamp of the upstream bank.

FIG. 11 shows a system built with the upstream bank (1) on a step (3) which is added to a slope (4) to raise the upstream bank (1) with respect to the downstream bank (2). This arrangement can be used to simplify construction as compared with two different slopes, and would also allow a smaller slope angle (5) to be selected for a given combination of velocity and submerged geometry.

Figure 12:
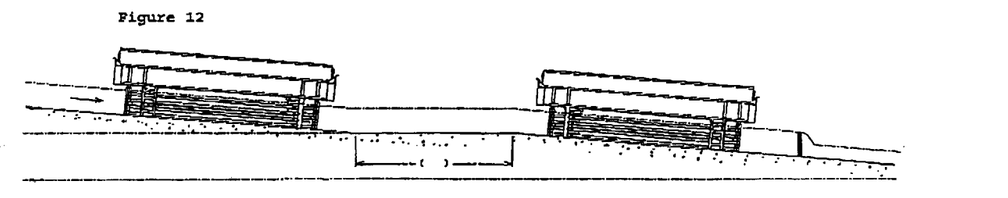
FIG. 12 shows a conceptual representation of two banks of modular assemblies in hydraulic series on the same slope angle with a horizontal section inserted between banks to allow the distance between banks to be increased without incurring an unnecessary increase in height.

FIG. 12 shows a horizontal section (3) between slopes (4) and (5). Such a section may be installed to prevent unnecessary elevation of the upstream bank (1) when the minimum distance between banks is limited by physical constraints. The addition of a horizontal section does not necessarily affect the water level profile (6) through the upstream (1) and downstream (2) banks. Slopes (4) and (5) may be at similar or different angles.

Figure 13:
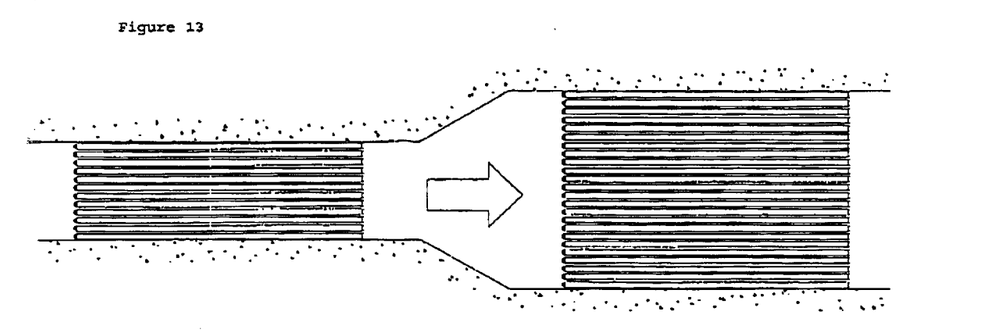
FIG. 13 shows a conceptual representation of two banks of modular assemblies in hydraulic series, the channel width being chosen for each bank such that velocity can be sufficiently reduced to recover some of the water level difference across the upstream bank and to reduce the water level difference across the downstream bank.

Adjustment of the channel width can also be used to change water level in a multi-bank system, as shown in FIG. 13. The upstream bank (1) is built with a narrower channel cross sectional area than the downstream bank (2). This results in a velocity decrease as fluid flows from (1) to (2), and a corresponding increase in water level through the bank. The ratio of widths may be selected based on the submerged geometry and flow rate such that the water level profile remains nearly constant.

Figure 14:
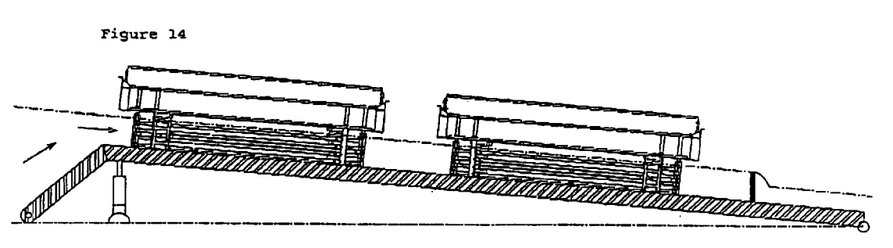
FIG. 14 shows a conceptual representation of two banks of modular assemblies in hydraulic series on a variable slope, adjusted by a mechanical actuator in response to measurements of flow or level, in order to maintain a desired water level profile.

A variable slope can be applied in response to changes in flow rate by adjusting either the UV equipment or the channel bottom, as shown in FIG. 14. Actuator (3) is adjusted in response to flow or water level measurements such that a desired water level profile (4) is maintained through the upstream (1) and downstream (2) banks. The pivot point (5) may be placed either downstream of the weir (6), between (6) and (2), or between (1) and (2). A hinged sliding baffle (7) is used to prevent fluid from passing beneath the adjustable channel bottom (8), which would result in poor disinfection performance and the accumulation of debris.

Any of the approaches described in any of the aforementioned Figures may be used either individually or in combination for overall management of water level within the UV reactor.

A system need not necessarily be designed with the slope chosen in order to maintain a water level profile parallel to the slope at maximum flow. As for systems built in horizontal channels, a certain amount of water level decrease is permissible while still maintaining disinfection performance. By sizing a system such that there is an allowable amount of water level decrease across all banks, typically an amount equal to one half the spacing between lamps plus one half the sleeve diameter, a smaller slope angle can be used. This results in a water level profile that is parallel to the channel bottom at less than the maximum flow rate, increasing the range of flow rates that can be optimally treated by the system. The ability to treat a wide range of flow rates is important, since waste water treatment plants rarely operate at their peak flow rate.

Since water level changes propagate upstream from a fixed point, as described above for weirs, during conditions of low flow the top lamps of the elevated upstream banks may become exposed. High lamp temperatures can occur as a result of insufficient cooling, which can compromise lamp life. One possible means of preventing this from occurring involves cooling of the top lamps, such as by a directed flow of a cooling fluid; for example, water or air. This can be in continuous operation, so that cooling is provided in the event of lamp exposure, or activated in response to a signal from a sensor. Sensors can function on the basis of detection of lamp temperature, water level, or UV intensity. If one or more sensors are employed, the signal may also be used to switch the affected lamps off to prevent damage and unnecessary operating expense. This can be used either alternatively to, or in conjunction with, lamp cooling to provide protection for exposed lamps.

Figure 15:
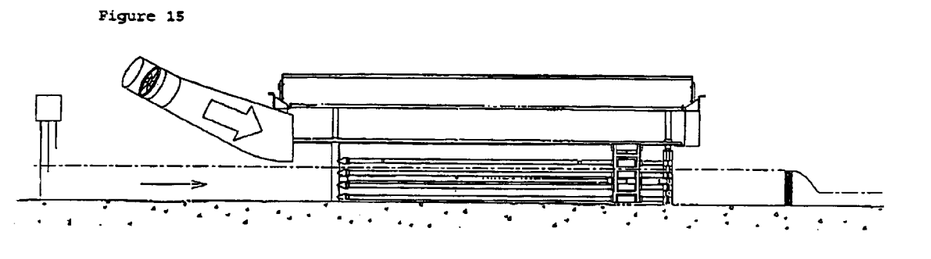
FIG. 15 shows a conceptual representation of a test conducted with one bank of modular assemblies having the top lamp exposed, a level sensor installed in order to switch off exposed lamps in response to a low water level condition, a fan installed in order to blow cooling air at exposed lamps in event of level sensor failure, and two temperature measurement points on the sleeve surface chosen in order to monitor the efficacy of air cooling on lamp temperature.

An experiment was conducted with a bank of eight modular assemblies in a test channel filled with water. A schematic diagram is shown in FIG. 15. A fan (2) was installed upstream of the bank (1) and ducted (3) so as to direct a flow (4) of ambient temperature (approximately 20° C.) air towards the top lamps (5) of the bank. Thermocouples were installed on the outside of the protective quartz sleeve surrounding each lamp at the upstream (6) and downstream (7) ends. One lamp at the center of the bank was fitted with thermocouples on both ends of the lamp, inside the sleeves. Temperature measurements were also made of the air exiting the bank (8). Air flow from the fan was measured using an annemometer. Intensity of one of the top lamps was measured with an IL-1700 radiometer to cross-reference lamp output with temperature measurements. A level sensor (9) was installed upstream of bank (1) to generate a low level signal which could be used to switch the top lamps off, turn the fans on, or both. A similar signal could be generated by a flow sensor or a temperature sensing device. These sensors could be positioned upstream of the bank, as shown, or at any other position on the system that generated an appropriate condition to provide a switching signal. Results of the test are shown in Table 6. Modules are labeled as M1 through M8 from left to right, looking in the direction of air flow.

When exposed to stagnant air, lamp temperatures in the center of the array reach 160° C. By cooling with air, the lamp temperature can be reduced to approximately 120° C. This is considered an acceptable lamp operating temperature to maintain lamp life for this type of lamp. Looking at the variation across a bank of eight modular assemblies, the average sleeve temperature varies by ±2.5° C. for the upstream measurement point (6) to ±6.0° C. for the downstream measurement point (7), in the 95% confidence interval. This is an acceptable interval across the bank, indicating that one fan is sufficient for implementation of air cooling on at least eight modular assemblies.

Elevation differences can be applied when UV systems are operated at high fluid velocities to prevent a "short circuit" over the top lamp, which would compromise the overall level of disinfection achieved. The data and figures show various system configurations that can be used. During periods of low flow, the elevation of the upstream bank may cause the top lamps of a modular assembly to become exposed, resulting in premature thermal failure. By using a cooling means, or by switching the top lamp off, such failures may be prevented. The novelty of the present invention is in the combination of these two concepts to allow the operation of UV systems at much higher fluid velocities than can be otherwise achieved, without compromising overall system performance, while maintaining lamp life during periods of low flow.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

TABLE 1

Summary of Data — Stepped Channel Testing

| | 1" Step (L/min) | | | 3" Step (L/min) | | | 5" Step (L/min) | | | | |
|---|---|---|---|---|---|---|---|---|---|---|---|
| | 2800 | 3600 | 4400 | 2800 | 3600 | 4400 | 3000 | 3600 | 4500 | 5500 | 6000 |
| First Bank | | | | | | | | | | | |
| Velocity (m/s) | 0.59 | 0.72 | 0.81 | 0.67 | 0.84 | 0.93 | 0.91 | 0.96 | 1.02 | 1.03 | 1.09 |
| Mid-point water level (in) | 12.75 | 13.1 | 14.1 | 13.5 | 14 | 15.5 | 13.8 | 15.1 | 16.5 | 17.25 | 18.5 |
| Water level difference (in) | 1 | 2 | 2.5 | 1.6 | 2.25 | 3.3 | 3.5 | 5.4 | 6.3 | 7.5 | 6.75 |
| Second Bank | | | | | | | | | | | |
| Velocity (m/s) | 0.58 | 0.76 | 0.94 | 0.58 | 0.74 | 0.92 | 0.63 | 0.79 | 0.97 | 1.1 | 1.09 |
| Mid-point water level (in) | 12 | 12.1 | 12.5 | 12 | 12.1 | 12.3 | 12 | 12.1 | 12.2 | 12.75 | 13.75 |
| Water level difference (in) | 1 | 2 | 4 | 0.8 | 1.8 | 3.45 | 0.8 | 0.3 | 1.1 | 5.5 | 7.5 |
| Total Head Lost (in) | 2 | 4 | 6.5 | 2.4 | 4 | 7 | 4.3 | 5.7 | 7.4 | 13 | 14.25 |
| Total Water Level Change (in) | 1.75 | 3.25 | 6.5 | 1.7 | 3.55 | 6.45 | 2.55 | 3.3 | 5.6 | 11.25 | 12.5 |

TABLE 2

Summary Table of Velocity Ranges for Different Step Heights

| Step Height (in) | Velocity Range (m/s) |
|---|---|
| No Step | 0–0.5 |
| 1 | 0.5–0.75 |
| 3 | 0.75–0.92 |
| 5 | 0.92–1 |

TABLE 3

Change of Water Level at 3 Velocities With 0% Slope

| Velocity (m/s) | Water Level Change (in.) |
|---|---|
| 0.3 | 0.4 |
| 0.6 | 1.1 |
| 0.9 | 3.1 |

TABLE 4

Change of Water Level at 0.9 m/s For 3 Different Slopes

| Slope (%) | Water Level Change (in.) |
|---|---|
| 0 | 3.1 |
| 1 | 0.2 |
| 2 | −1.6 |

TABLE 5

Change of Water Level at 0.9 m/s for 2 Different Slopes and Less Restrictive Submerged Geometry

| Slope (%) | Water Level Change (in.) |
|---|---|
| 0 | 1.5 |
| 1 | −0.2 |

TABLE 6

Lamp Cooling With Air

| Air Vel. (Fpm) | Temperature (° C.) Sleeve Temp. (upstream side, close to fan) | | | | | | | |
|---|---|---|---|---|---|---|---|---|
| | M1 | M2 | M3 | M4 | M5 | M6 | M7 | M8 |
| In Water | 45 | 41 | 46 | 40 | 48 | 51 | 53 | 43 |
| 0 | 137 | 141 | 144 | 112 | 132 | 128 | 134 | 136 |
| 368 | 106 | 110 | 114 | 102 | 116 | 110 | 116 | 119 |
| 368 | 104 | 109 | 113 | 101 | 115 | 109 | 115 | 117 |
| 368 | 107 | 111 | 115 | 102 | 114 | 110 | 115 | 117 |
| 460 | 97 | 101 | 105 | 99 | 112 | 108 | 114 | 113 |
| 460 | 98 | 102 | 106 | 95 | 112 | 107 | 113 | 112 |
| 735 | 72 | 75.5 | 79 | 72 | 87 | 85 | 89 | 85 |
| 827 | 69 | 72 | 75 | 75 | 83 | 82 | 86 | 82 |
| 919 | 69 | 72 | 75 | 77 | 82 | 81 | 86 | 82 |

| Air Vel. (Fpm) | Temperature (° C.) Sleeve Temp. (downstream side, far from fan) | | | | | | | |
|---|---|---|---|---|---|---|---|---|
| | M1 | M2 | M3 | M4 | M5 | M6 | M7 | M8 |
| In Water | 38 | 37 | 40 | 38 | 40 | 40 | 41 | 36 |
| 0 | 137 | 136 | 131 | 90 | 132 | 116 | 113 | 117 |
| 368 | 146 | 161 | 147 | 102 | 142 | 123 | 123 | 126 |
| 368 | 142 | 147 | 142 | 102 | 140 | 122 | 122 | 125 |
| 368 | 137 | 145 | 133 | 103 | 137 | 124 | 123 | 126 |
| 460 | 128 | 127 | 126 | 61 | 138 | 124 | 122 | 121 |
| 460 | 128 | 122 | 125 | 77 | 136 | 122 | 121 | 121 |
| 735 | 101 | 95 | 101 | 60 | 115 | 108 | 108 | 107 |
| 827 | 97 | 91 | 97 | 63 | 110 | 106 | 107 | 105 |
| 919 | 97 | 90 | 95 | 67 | 114 | 107 | 108 | 105 |

| Air Vel. (Fpm) | Temperature (° C.) Lamp | | Air out | Intensity[1] M8 |
|---|---|---|---|---|
| | M4 | M4 | | |
| In Water | 91 | 93 | 18 | |
| 0 | 158 | 152 | 18 | 0.256 |
| 368 | 147 | 157 | 18 | 0.218 |
| 368 | 147 | 156 | 19 | 0.220 |
| 368 | 147 | 157 | 19 | 0.226 |
| 460 | 144 | 142 | 19 | 0.260 |
| 460 | 141 | 143 | 19 | 0.261 |
| 735 | 122 | 127 | 20 | 0.365 |
| 827 | 123 | 128 | 21 | 0.383 |
| 919 | 124 | 127 | 21 | 0.392 |

[1]Units: mW/cm$^2$

What is claimed is:

1. A fluid treatment system comprising:
   at least two radiation sources disposed in an open channel irradiation zone, one of the at least two radiation sources being disposed above another of the at least two radiation sources, the irradiation zone having a fluid inlet which is elevated with respect to a fluid outlet; and
   said one of the at least two radiation sources being configured to be switched off during a period of low fluid flow, while said another of the at least two radiation sources is not switched off.

2. The fluid treatment system defined in claim 1, wherein the at least two radiation sources are disposed substantially parallel to the direction of flow of fluid to the open irradiation zone.

3. The fluid treatment system defined in claim 1, wherein the at least two radiation sources are disposed substantially transverse to the direction of flow of fluid to the open irradiation zone.

4. The fluid treatment system defined in claim 1, wherein a plurality of top radiation sources are configured to be switched off during a period of low fluid flow.

5. The fluid treatment system defined in claim 1, wherein the open channel comprises a sloped surface disposed between the fluid inlet and the fluid outlet.

6. The fluid treatment system defined in claim 1, wherein the open channel comprises a plurality of sloped surfaces disposed between the fluid inlet and the fluid outlet.

7. The fluid treatment system defined in claim 6, wherein the sloped surfaces have substantially the same slope.

8. The fluid treatment system defined in claim 6, wherein the sloped surfaces have substantially different slopes.

9. The fluid treatment system defined in claim 5, wherein the sloped surface is adjustable.

10. The fluid treatment system defined in claim 5, wherein the sloped surface connects the fluid inlet and the fluid outlet.

11. The fluid treatment system defined in claim 5, wherein the sloped surface comprises a slope of at least about 0.2%.

12. The fluid treatment system defined in claim 5, wherein the sloped surface comprises a slope in the range of from about 0.2% to about 6.0%.

13. The fluid treatment system defined in claim 5, wherein the sloped surface comprises a slope in the range of from about 0.2% to about 3.0%.

14. The fluid treatment system defined in claim 5, wherein the sloped surface comprises a slope in the range of from about 0.5% to about 2.5%.

15. The fluid treatment system defined in claim 5, wherein the sloped surface comprises a slope in the range of from about 1.0% to about 2.0%.

16. The fluid treatment system defined in claim 1, wherein the at least one radiation source is substantially parallel to the sloped surface.

17. The fluid treatment system defined in claim 1, wherein the open channel comprises at least one stepped platform disposed between the fluid inlet and the fluid outlet, the at least one stepped platform comprising the at least one radiation source.

18. The fluid treatment system defined in claim 17, wherein the at least one stepped platform comprises a height in the range of from about 0.5 to about 7.0 inches.

19. The fluid treatment system defined in claim 17, wherein the at least one stepped platform comprises a height in the range of from about 0.5 to about 5.0 inches.

20. The fluid treatment system defined in claim 17, wherein the at least one stepped platform comprises a height in the range of from about 1.0 to about 4.0 inches.

21. The fluid treatment system defined in claim 17, wherein the at least one stepped platform comprises a height in the range of from about 1.0 to about 3.0 inches.

22. The fluid treatment system defined in claim 17, wherein the open channel comprises a plurality of stepped platforms disposed between the fluid inlet and the fluid outlet.

23. The fluid treatment system defined in claim 17, wherein the at least one radiation source is substantially parallel to the stepped platform.

24. The fluid treatment system defined in claim 1, wherein the open channel comprises a combination of at least one sloped surface and at least one stepped platform disposed between the fluid inlet and the fluid outlet.

25. The fluid treatment system defined in claim 1, comprising a plurality of radiation sources arranged in an array.

26. The fluid treatment system defined in claim 25, wherein the array comprises a plurality of radiation sources disposed in a radiation source module.

27. The fluid treatment system defined in claim 25, wherein the array comprises a plurality of radiation source modules.

28. The fluid treatment system defined in claim 27, wherein the plurality of radiation source modules are arranged in series to fluid flow through the system.

29. The fluid treatment system defined in claim 27, wherein the plurality of radiation source modules are arranged in parallel to fluid flow through the system.

30. The fluid treatment system defined in claim 1, wherein the open irradiation zone comprises a substantially constant width.

31. The fluid treatment system defined in claim 1, wherein the open irradiation zone comprises a variable width.

32. The fluid treatment system defined in claim 27, wherein the plurality of radiation source modules are arranged in series and in parallel to fluid flow through the system.

33. A fluid treatment system comprising:
   an array of radiation sources disposed in an open channel, a top one of said radiation sources being configured to be switched off during a period of low flow when a lower one of said radiation sources is switched on; and
   an upstream end of the open channel adjacent an upstream end of the array being elevated with respect to a downstream end of the open channel adjacent a downstream end of the array.

34. The fluid treatment system defined in claim 33, wherein the array of radiation sources is disposed substantially parallel to the direction of flow of fluid to the open irradiation zone.

35. The fluid treatment system defined in claim 33, wherein the array of radiation sources is disposed substantially transverse to the direction of flow of fluid to the open irradiation zone.

36. The fluid treatment system defined in claim 33, wherein a plurality of top radiation sources are configured to be switched off during a period of low fluid flow.

37. The fluid treatment system defined in claim 33, wherein the open channel comprises a continuous open channel.

38. The fluid treatment system defined in claim 33, wherein the open channel comprises a sloped surface disposed between the fluid inlet and the fluid outlet.

39. The fluid treatment system defined in claim 33, wherein the open channel comprises a plurality of sloped surfaces disposed between the fluid inlet and the fluid outlet.

40. The fluid treatment system defined in claim 39, wherein the sloped surfaces have substantially the same slope.

41. The fluid treatment system defined in claim 39, wherein the sloped surfaces have substantially different slopes.

42. The fluid treatment system defined in claim 38, wherein the sloped surface is adjustable.

43. The fluid treatment system defined in claim 38, wherein the sloped surface connects the fluid inlet and the fluid outlet.

44. The fluid treatment system defined in claim 38, wherein the sloped surface comprises a slope of at least about 0.2%.

45. The fluid treatment system defined in claim 38, wherein the sloped surface comprises a slope in the range of from about 0.2% to about 6.0%.

46. The fluid treatment system defined in claim 38, wherein the sloped surface comprises a slope in the range of from about 0.2% to about 3.0%.

47. The fluid treatment system defined in claim 38, wherein the sloped surface comprises a slope in the range of from about 0.5% to about 2.5%.

48. The fluid treatment system defined in claim 38, wherein the sloped surface comprises a slope in the range of from about 1.0% to about 2.0%.

49. The fluid treatment system defined in claim 38, wherein the radiation sources are substantially parallel to the sloped surface.

50. The fluid treatment system defined in claim 33, wherein the open channel comprises at least one stepped platform disposed between the fluid inlet and the fluid outlet, the at least one stepped platform comprising the array of radiation sources.

51. The fluid treatment system defined in claim 50, wherein the at least one stepped platform comprises a height in the range of from about 0.5 to about 7.0 inches.

52. The fluid treatment system defined in claim 50, wherein the at least one stepped platform comprises a height in the range of from about 0.5 to about 5.0 inches.

53. The fluid treatment system defined in claim 50, wherein the at least one stepped platform comprises a height in the range of from about 1.0 to about 4.0 inches.

54. The fluid treatment system defined in claim 50, wherein the at least one stepped platform comprises a height in the range of from about 1.0 to about 3.0 inches.

55. The fluid treatment system defined in claim 33, wherein the open channel comprises at least one stepped platform disposed between the fluid inlet and the fluid outlet, the at least one stepped platform comprising the array.

56. The fluid treatment system defined in claim 33, wherein the open channel comprises at plurality of stepped platforms disposed between the fluid inlet and the fluid outlet.

57. The fluid treatment system defined in claim 56, wherein each stepped platform comprises an array of radiation sources.

58. The fluid treatment system defined in claim 33, wherein the open channel comprises a combination of at least one sloped surface and at least one stepped platform.

59. The fluid treatment system defined in claim 38, wherein the at least one radiation source is substantially parallel to the sloped surface.

60. The fluid treatment system defined in claim 33, wherein the array comprises a plurality of radiation sources disposed in a radiation source module.

61. The fluid treatment system defined in claim 60, wherein the array comprises a plurality of radiation source modules.

62. The fluid treatment system defined in claim 61, wherein the plurality of radiation source modules are arranged in series to fluid flow through the system.

63. The fluid treatment system defined in claim 33, wherein the open channel comprises a substantially constant width.

64. The fluid treatment system defined in claim 33, wherein the open channel comprises a variable width.

65. The fluid treatment system defined in claim 61, wherein the plurality of radiation source modules are arranged in parallel in fluid flow through the system.

66. The fluid treatment system defined in claim 61, wherein the plurality of radiation source modules are arranged in series and in parallel to fluid flow through the system.

67. A fluid treatment system comprising:
a plurality of serially disposed open channel irradiation zones which are elevated with respect to one another thereby substantially normalizing the fluid level with respect to the top of each irradiation zone; and
two radiation sources disposed in at least one of said plurality of serially disposed open channel irradiation zones, a top radiation source being configured to be switched off during a period of low flow while a lower radiation source is not switched off.

68. A fluid treatment system comprising:
a first irradiation zone and a second irradiation zone disposed at different heights with respect to one another in an open channel such that the fluid level is substantially normalized with respect to the top of each of the first irradiation zone and the second irradiation zone; and
two radiation sources disposed in said first irradiation zone, a top radiation source being configured to be switched off during a period of low flow while a lower radiation source remains on.

69. The fluid treatment system defined in claim 68, wherein the first irradiation zone is stepped with respect to the second irradiation zone.

70. The fluid treatment system defined in claim 68, wherein the first irradiation zone is sloped with respect to the second irradiation zone.

71. A fluid treatment system comprising a canal for receiving a fluid to be treated, a first upstream irradiation zone and a second downstream irradiation zone which is elevated with respect to the first upstream irradiation zone.

72. The fluid treatment system defined in claim 71, wherein the first irradiation zone is stepped with respect to the second irradiation zone.

73. The fluid treatment system defined in claim 71, wherein the first irradiation zone is sloped with respect to the second irradiation zone.

* * * * *